United States Patent
Ng

(10) Patent No.: US 6,626,347 B2
(45) Date of Patent: Sep. 30, 2003

(54) FASTENER RETAINING DEVICE FOR FASTENER DRIVER

(76) Inventor: Kim Kwee Ng, 10 Malibu La., Centereach, NY (US) 11720-3042

( * ) Notice: Subject to any disclaimer, the term of this patent is extended or adjusted under 35 U.S.C. 154(b) by 0 days.

(21) Appl. No.: 10/068,975

(22) Filed: Feb. 11, 2002

(65) Prior Publication Data

US 2003/0150897 A1 Aug. 14, 2003

(51) Int. Cl.⁷ .............................................. B25C 1/02
(52) U.S. Cl. ........................ 227/147; 227/119; 227/149
(58) Field of Search ............................... 227/113, 119, 227/147, 149, 175.1; 81/452; 606/104

(56) References Cited

U.S. PATENT DOCUMENTS

| | | | | |
|---|---|---|---|---|
| 916,026 A | * | 3/1909 | Sasseman | 227/149 |
| 1,549,413 A | * | 8/1925 | Greet | 81/452 |
| 1,712,196 A | * | 5/1929 | Burger et al. | 81/452 |
| 1,779,339 A | * | 10/1930 | Sokoloff | 81/452 |
| 2,248,054 A | * | 7/1941 | Becker | 81/457 |
| 2,532,972 A | * | 12/1950 | Vertin | 81/443 |
| 2,579,438 A | * | 12/1951 | Longfellow | 81/453 |
| 2,954,809 A | * | 10/1960 | Loewy | 81/452 |
| 2,973,527 A | * | 3/1961 | Maynard et al. | 7/167 |
| 3,060,440 A | * | 10/1962 | Pfaff et al. | 227/147 |
| 3,245,446 A | * | 4/1966 | Morifuji | 81/452 |
| 3,604,487 A | * | 9/1971 | Gilbert | 81/443 |
| 4,195,762 A | * | 4/1980 | Burton | 227/156 |
| 4,263,903 A | * | 4/1981 | Griggs | 606/75 |
| 4,363,250 A | * | 12/1982 | Suga | 81/455 |
| 4,438,769 A | * | 3/1984 | Pratt et al. | 227/175.1 |
| 4,461,418 A | * | 7/1984 | Schaefer | 227/147 |
| 4,581,963 A | * | 4/1986 | Kim | 81/452 |
| 4,763,548 A | * | 8/1988 | Leibinger et al. | 81/453 |
| 4,901,712 A | * | 2/1990 | Voegell et al. | 606/75 |
| 5,649,931 A | * | 7/1997 | Bryant et al. | 606/104 |
| 5,971,987 A | * | 10/1999 | Huxel et al. | 606/73 |

* cited by examiner

Primary Examiner—Stephen F. Gerrity
Assistant Examiner—Nathaniel Chukwurah

(57) ABSTRACT

The retention device for retaining a fastener comprises an outer tubular shaft slidably disposed upon an inner tubular shaft. Extending from the distal end of the inner tubular shaft is a plurality of resilient gripping members, each having an arcuated portion protruding outwardly from the cylindrical axis of the inner tubular shaft. The outer tubular shaft, having a conically tapered inner bore, is longitudinally slid along the inner tubular shaft to press inwardly the arcuated portions so that the gripping members grasp a fastener at the distal ends thereof. The outer tubular shaft can be internally threaded to provide varying strength for retaining or releasing the fastener. A restraining resilient member is provided to prevent the retention device from falling off from the fastening tool by engaging an annular flange disposed upon the shank of the fastening tool. Another retention device, comprising two independent sets of gripping members for use separately in combination with two co-operating outer tubular shafts, is employed to provide multiple contact points at the head and shank of the fastener for better alignment and improved holding capability.

18 Claims, 4 Drawing Sheets

FASTENER RETAINING DEVICE FOR FASTENER DRIVER

BACKGROUND OF INVENTION

The invention relates generally to fasteners and fastener drivers and particularly to those utilizing a retention device to retain the fastener in position for positive engagement into its target location.

It has often happened that a bolt or a screw is required to be inserted into an area that is difficult to access. A retaining device is usually needed to save time and effort to bring the bolt or screw into its target location. In medical surgery, the surgical area in which a bone screw is to be introduced is usually very narrow. It is often difficult to hold the bone screw by hand or by other tool so that the bone screw can be accurately and securely fastened into the targeted area.

There are many prior art screwdrivers which address the aforementioned difficulty in many different ways. These include, but not limited to a magnetized screwdriver, a gripper of different designs and a tubular shaft for guiding the screw.

U.S. Pat. No. 6,189,422 discloses a screwdriver having a retention device capable of retaining a bone screw before inserting the screw into a human or an animal body. The retention device includes a clamping gripper mounted at the distal end of an inner tubular shaft which surrounds the shaft of the screwdriver. An actuation device is provided on the handle of the screwdriver to longitudinally displace an outer tubular shaft so that the outer tubular shaft is moved relative to the inner tubular shaft and over the clamping gripper to close the jaws of the clamping gripper, thereby holding the screw firmly without wobbling. However, the retention device is relatively complicated in terms of the needed disassembly and assembly that is required for disinfection.

U.S. Pat. No. 4,016,913 discloses a holding device comprising a sleeve adapted to fit over the shank of a screwdriver. A pair of diverging arms is mounted at the distal end of the sleeve. A pair of coil springs extending between the diverging arms is adapted to grip the shank of a fastener. Use of bulky items like the coil springs and diverging arms often renders the retention device inadequate for use in a confined space where the fastener is to be located for insertion.

One of the disadvantages of these prior art devices utilizing a gripper is that the gripper can only assume two distinct positions while holding the screw in place in its jaws. The jaws are either open very widely or closed very tightly. The range on the sizes of the screw that can be covered by a specific retention device is limited. The holding strength for retaining or releasing the screw in its place cannot be varied. Moreover, any alignment error of the screw while being held by the gripper cannot be easily corrected.

The screw usually cannot be released gently from the clamping gripper in many of the prior art retention devices.

The retention means of some of the prior art devices for retaining a bolt or screw are quite complicated. The magnetic strength of a magnetized screwdriver is known to decay over time. Furthermore the magnetized screwdriver is often inadequate for some dedicated works, especially for a fastener which is made of a plastic material or of a non-ferromagnetic metal.

Other retention devices are only applicable to some specific applications of introducing a screw for insertion into a workpiece. An object of this invention is to provide a holding device that is simpler in construction, which usually translates into a lower cost of manufacture. Some of the inventive devices described hereinafter can easily be made by molding, further reducing the production cost of the retention device.

Another object is to have a retention device for use with a screwdriver that can be easily assembled and disassembled. A fast disassembly and assembly feature of the retention device is especially important for easy cleaning in medical surgery so that the various components of the retention device and the screwdriver can be thoroughly, readily and quickly sterilized before an operation.

An object of this invention is to provide a means of manipulating the size of the gripping jaw's opening, thus increasing the range of sizes of bolts and screws the retention device can hold for insertion into a normally inaccessible area of a workpiece. Such a retention device also provides varying strength for holding or releasing the fastener gently.

A still further object is to provide multiple contact points at different parts of the fastener for better screw alignment and improved holding capability, thus further preventing the fastener from dislodging by a sideward displacement during a fastening process. Initial alignment error of the fastener can easily be corrected since the holding strength on the fastener can be varied. The improved retention device is still relatively simple to produce, operate and assemble.

Many of the prior art retention devices are very complicated in design, usually involving many structural components. Some of the retention systems have obvious advantages, however, are expensive to manufacture.

Accordingly, it is the object of the present invention to provide an improved retention device which is simpler to manufacture at a lower cost and easier to operate than the prior art retention means.

SUMMARY OF INVENTION

The retention device for retaining a fastener comprises an outer tubular shaft slidably disposed upon an inner tubular shaft. Extending from the distal end of the inner tubular shaft is a plurality of resilient gripping members, each having an arcuated section protruding radially away from the axis of the inner tubular shaft. A resilient restraining member mounted on the opposite end of the inner tubular shaft engages an annular flange disposed upon the shank of the fastening tool to prevent the inner tubular shaft from falling off from the fastening tool.

The outer tubular shaft, a portion of which has an inner through bore in a conical shape, is moved along the inner tubular shaft and over the arcuated sections to press in the gripping members to grasp a fastener at the distal end. In another embodiment of the invention, the inner tubular shaft is internally threaded. The holding strength for retaining or releasing the fastener at the distal ends of the gripping members can be gradually varied by rotating the outer tubular shaft with respect to the inner tubular shaft.

In yet another embodiment of the invention, the outer tubular shaft and the inner tubular shaft are both mounted on the handle of the fastening tool for easy handling by simply rotating the outer tubular shaft to engage the fastener for insertion into the workpiece. The fastener can be released gently in a controllable fashion. A simple retention device, comprising mainly an outer tubular shaft and a plurality of gripping members mounted on an inner tubular shaft is also discussed. The device preferably provides a resilient restraining member for engaging either an annular flange on the shank, or an annular recess embedded in the shank, to prevent the retention device from falling off from the fastening tool.

Another retention device, comprising two independent sets of gripping members for use separately in combination with two co-operating outer tubular shafts, is employed to provide multiple contact points at different parts of the fastener, namely at the head and shank of the fastener for better alignment and improved holding capability.

DETAILED DESCRIPTION

A more complete understanding of my invention may be obtained through a study of this description when taken together with the appended drawings, wherein like reference symbols refer to like elements of the drawings.

Figure 1:
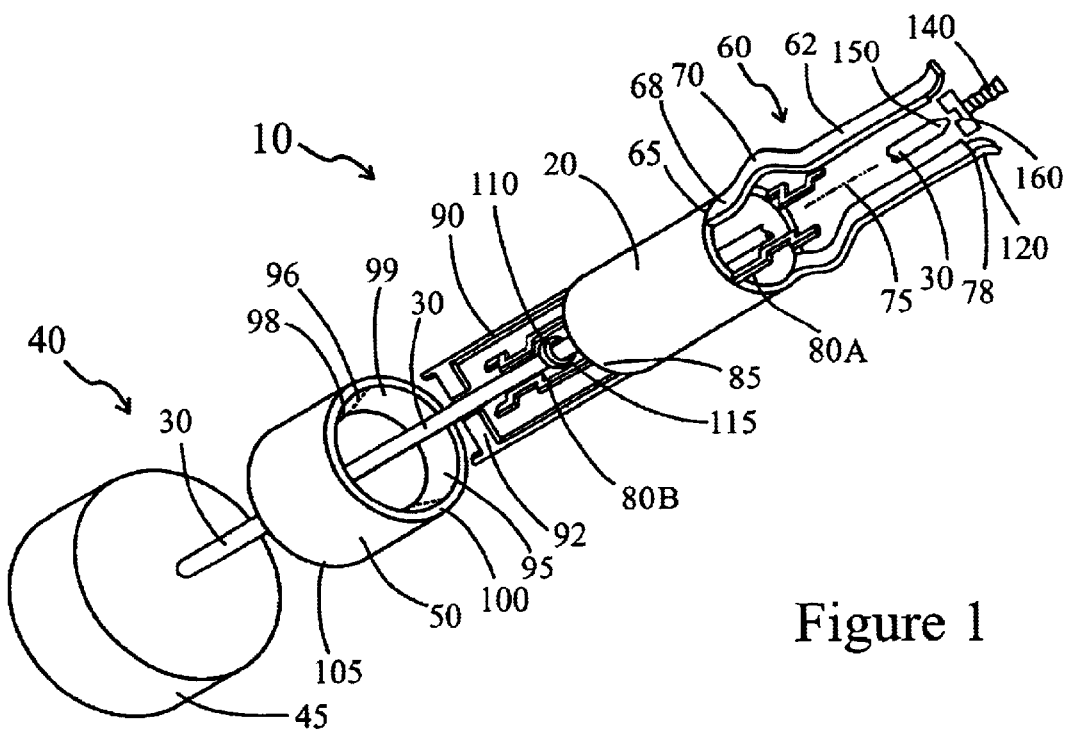
FIG. 1 is a simplified diagram of a first preferred embodiment showing an outer tubular shaft and an inner tubular shaft with a pair of gripping jaws.

Referring now to the first preferred embodiment of the invention shown in FIG. 1, wherein a retention device 10 comprises an inner tubular shaft 20 receivable upon an elongated shank 30 of a fastening tool 40 having a handle 45, and an outer tubular shaft 50 slidably disposed upon the inner tubular shaft 20.

The fastening tool 40 can be a flat blade screwdriver, a Phillips screwdriver, a power-driven screwdriver or the like. Extended from the distal end 65 of the inner tubular shaft 20 is a clamping gripper 60, which comprises generally a pair of resilient deformable opposing gripping members 62. Each of the gripping members 62 has on its elongated handle 68 a curved arcuated portion 70 protruding outward from a central axis, which is the cylindrical axis 75 of the inner tubular shaft 20. At the distal end of each gripping member 62 is a gripping jaw 78.

A plurality of resilient u-shaped members 80A and 80B are respectively mounted at the distal end 65 in between the gripping members 62 and at the proximal end 85 of the inner tubular shaft 20. U-shaped members 80A and 80B slidingly engage the shank 30 of the fastening tool 40, so that the inner tubular shaft 20 is longitudinally slidable and rotatable about the shank 30.

A pair of resilient beams 90, each comprising an end portion 92 engaging the shank 30, are mounted at the proximal end 85 of the inner tubular shaft 20.

Beams 90 are shown to have been displaced with respect to the u-shaped members 80B, so that a clearer view of all the components in the diagram can be presented.

The outer tubular shaft 50, having an inner through bore 95, comprises a conically tapered bore portion denoted by dashed lines 96 and a substantially uniform end bore portion 98. Tapered bore portion 96 has an inner diameter which is decreasing with depth as measured in a direction from end 100 to the opposite end 105 of the outer tubular shaft 50. End bore portion 98 is substantially constant in its inner diameter and is slidably disposed upon the inner tubular shaft 20. The outer tubular shaft 50 is inserted onto the shank 30 of the fastening tool 40, followed by a flexible annular ring or flange 110 slidably mounted and held frictionally onto the shank 30. The inner tubular shaft 20 is inserted next and mounted along the shank 30, with the u-shaped members 80B and beams 90 lifted away from shank 30 so that the annular flange 110 on shank 30 is positioned between the u-shaped members 80A and the u-shaped members 80B.

The linear movement of the inner tubular shaft 20 is constrained at position 115 by the annular flange 110 on shank 30. The annular flange 110 blocks the u-shaped members 80B of the inner tubular shaft 20 at position 115, preventing the inner tubular shaft 20 from coming off unless the u-shaped members 80B and beams 90 are lifted away from shank 30. Annular flange 110, which can also be a ridge on the shank 30, serves as a blocking and passive restraining means to prevent the passage of the inner tubular shaft 20.

The outer tubular shaft 50 is longitudinally slid along the inner tubular shaft 20 to come into engagement with the arcuated portion 70. The interior bore wall surface 99 of the inner tapered bore 96 presses the arcuated portion 70 of the handle 68 inwardly towards the cylindrical axis 75 of the inner tubular shaft 20, thereby moving the opposing gripping jaws 78 of the gripping members 62 radially towards each other. Gripping jaws 78 are eventually closed from an initially open position to finally grasp a bolt 140 in a closed position.

With the bolt 140 being retainably held firmly in place by the clamping gripper 60, the engaging bit in the driver head 150 of the fastening tool 40 starts the fastening process by engaging a receptacle 160 in the head of the bolt 140. The tips at the distal ends 120 of the gripping members 62 are radially bent or spread outwardly away from the cylindrical axis 75 so that the bolt 140 can be fastened completely into a workpiece (not shown).

In its preferred mode of fabrication, the clamping gripper 60 may be fabricated using a resilient material such as molded plastic, fiber glass or other sufficiently strong material to provide suitable spring resiliency for the gripping jaws.

Figure 2:
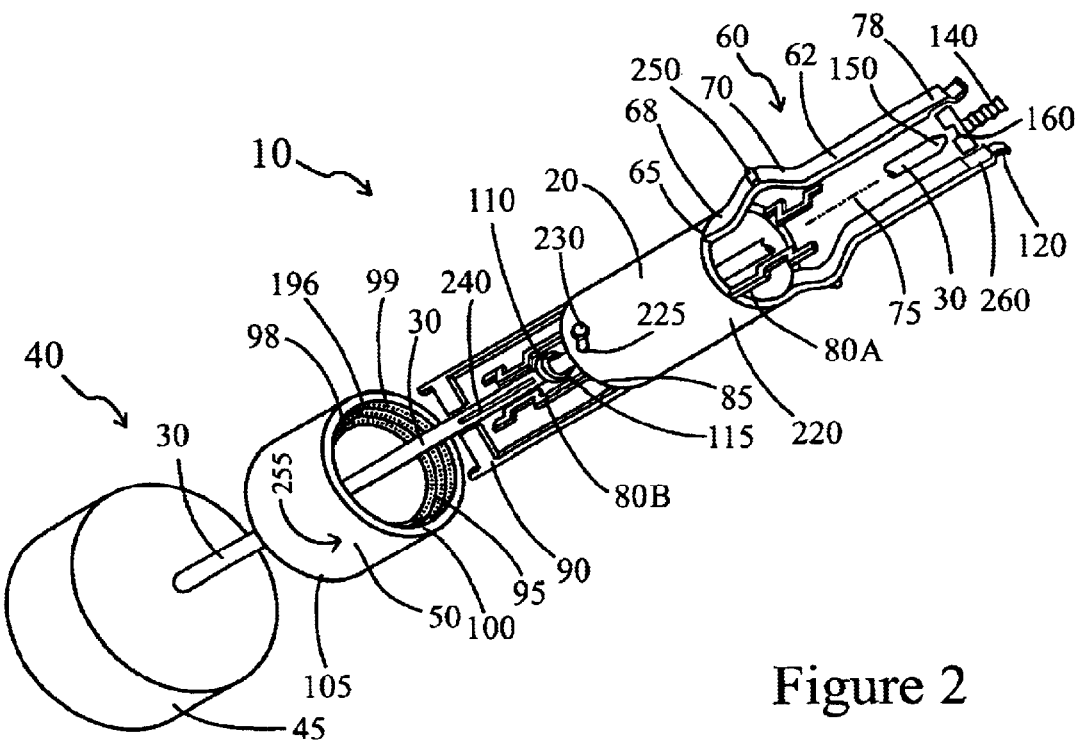
FIG. 2 is a simplified diagram of a second preferred embodiment showing an internally threaded outer tubular shaft.

Referring now to the second preferred embodiment of the invention shown in FIG. 2, wherein a retention device 10 comprises an inner tubular shaft 20 enclosing an elongated shank 30 of a fastening tool 40 having a handle 45, and an outer tubular shaft 50 slidably disposed upon the inner tubular shaft 20.

Extending from the distal end 65 of the inner tubular shaft 20 is a clamping gripper 60, which comprises a pair of resilient opposing gripping members 62.

Each of the gripping members 62 has on its elongated handle 68 an arcuated portion 70 protruding radially outward from a cylindrical axis 75 of the inner tubular shaft 20.

A plurality of resilient u-shaped members 80A and 80B are respectively mounted at the distal end 65 and at the proximal end 85 of the inner tubular shaft 20. U-shaped members 80A and 80B slidingly engage the shank 30 of the fastening tool 40, so that the inner tubular shaft 20 is slidable longitudinally and rotatable about the shank 30. A pair of resilient beams 90 extending from the proximal end 85 of the inner tubular shaft 20 engages the shank 30 for linear movement along shank 30.

The outer tubular shaft 50, having an inner through bore 95 comprises a conically internally threaded tapered bore portion denoted by dashed lines 196 and a substantially uniform end bore portion 98. Threaded tapered bore portion 196 has an inner diameter which is decreasing with depth as measured in a direction from end 100 to the opposite end 105 of the outer tubular shaft 50.

Threaded tapered bore portion 196 is denoted by an array of alternate solid lines and dashed lines representing respectively the ridges and furrows of the interior portion of the inner threaded tapered bore 196. End bore portion 98 is substantially constant in the inner diameter and is slidably disposed upon the inner tubular shaft 20.

An annular flange 110 is provided on shank 30 and is positioned between the u-shaped members 80A and the u-shaped members 80B. The linear movement of the inner tubular shaft 20 is constrained at position 115 by the annular flange 110 on shank 30. The annular flange 110 prevents the inner tubular shaft 20 from falling off from shank 30 unless the u-shaped members 80B and beams 90 are lifted radially away from shank 30.

The cylindrical wall 220 of the inner tubular shaft 20 is provided with a threaded through opening 225 through which a releasable fastener 230 may pass into engagement with the shank 30 of the fastening tool 40. The tip of the fastener 230 engaging the shank 30 frictionally prevents the inner tubular shaft 20 from rotating with respect to shank 30 when the inner tubular shaft 20 needs to be held steady for the smooth relative rotation of the outer tubular shaft 50 and the inner tubular shaft 20.

The fastener 230, serving as a locking means, engages a longitudinal channel 240 provided on the shank 30 of the fastening tool 40. The fastener 230 is insertable into and removable from the cylindrical wall 220 when the outer tubular shaft 50 is positioned to rotate about the inner tubular shaft 20.

A segmented guiding ridge 250, engageable with the threaded interior tapered wall 99 of the outer tubular shaft 50, is mounted on the outer surface of the arcuated sections 70 of clamping gripper 60. The outer tubular shaft 50 is slid along the inner tubular shaft 20 to come into engagement with the guiding ridge 250 on the arcuated portion 70 of the clamping gripper 60. The outer tubular shaft 50 is rotated with respect to the inner tubular shaft 20 in the direction denoted by a curved arrow 255. The interior tapered wall 99 continually presses inwardly on the arcuated portion 70 of the handle 68 towards the cylindrical axis 75, which is now the axis of rotation of the outer tubular shaft 50, until the gripping jaws 78 of the clamping gripper 60 is finally closed to grasp a fastener 140. Further tightening can be done by simply rotating the outer tubular shaft 50 about the inner tubular shaft 20 in the direction 255 as shown in FIG. 2.

The gripping jaws 78 comprises a gripping portion section 260, adapted to hold the head of the fastener 140 to prevent slipping and to securely grasp the fastener 140 before insertion into a workpiece (not shown).

The fastener 140 can be released gently by rotating the outer tubular shaft 50 with respect to the inner tubular shaft 20 in a second direction opposite to the curved arrow shown as 255. It is clear that the variation in the conically tapered interior wall 99 of the through bore 95 allows for use with fasteners of a wide variety of sizes.

Figure 3:
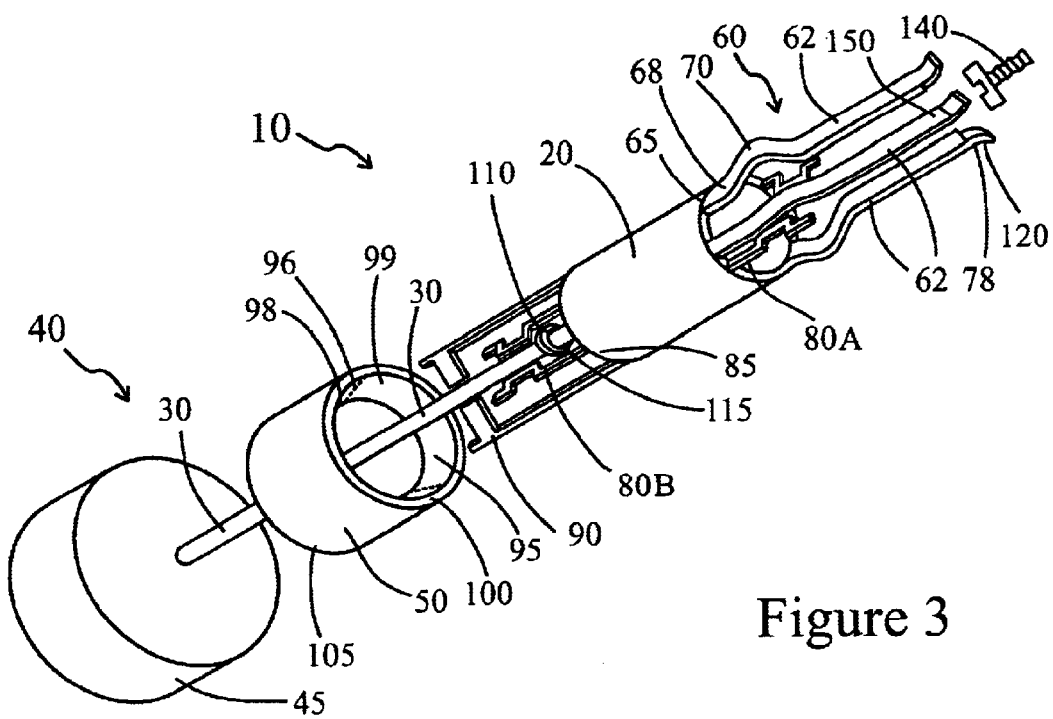
FIG. 3 is a simplified diagram of a third preferred embodiment having a plurality of jaws.

Referring now to the third preferred embodiment of the invention shown in FIG. 3, wherein a retention device 10 comprises of an inner tubular shaft 20 having a plurality of resilient gripping members 62 mounted at a distal end 65 for grasping a fastener 140. Gripping members 62 are preferably arranged circumferentially with axial symmetry about a cylindrical axis 75 of the inner tubular shaft 20. The inner cylindrical tapered wall 99 of the outer tubular shaft 50 presses inwardly the arcuated portion 70 of the gripping members 62 towards the cylindrical axis 75 of the inner tubular shaft 20. The jaws 78 of the gripping members 62 finally grasp a fastener 140 for insertion into a workpiece (not shown). The functions of the u-shaped members 80A, 80B and the annular flange 110 in the diagram are described in detail in the foregoing embodiments.

Figure 4:
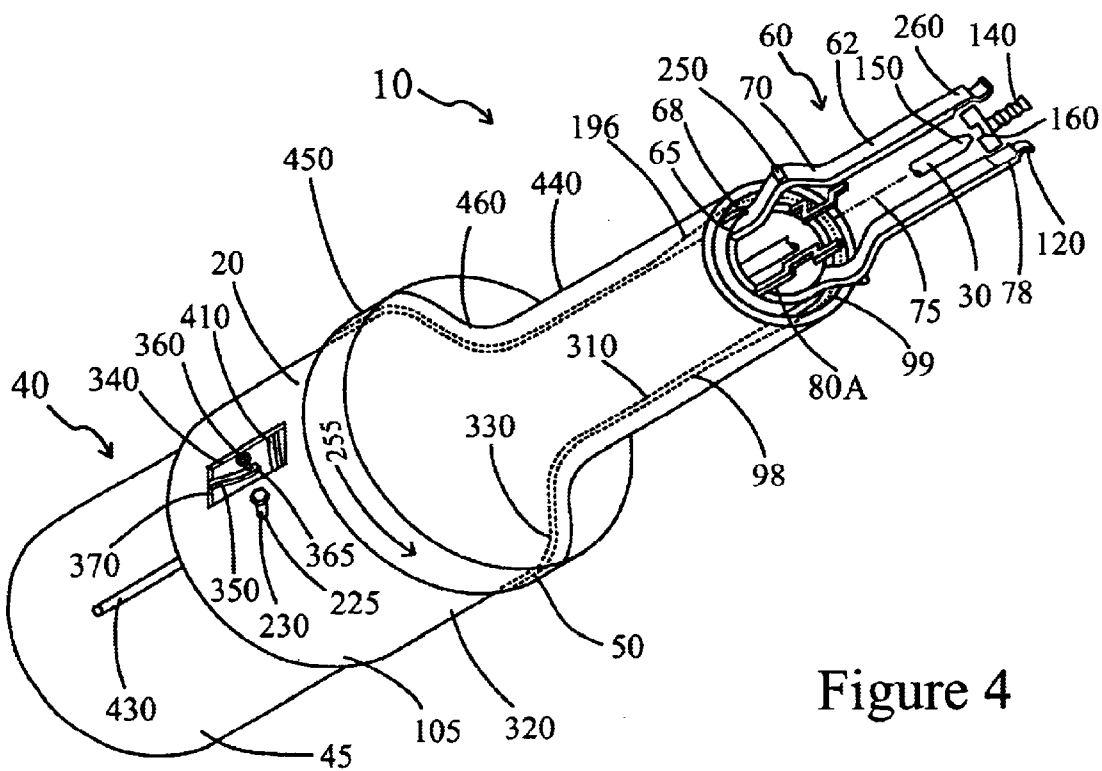
FIG. 4 is a simplified diagram of a fourth preferred embodiment showing an inner tubular shaft being mounted on the handle of the fastening tool.

Referring now to the fourth preferred embodiment of the invention shown in FIG. 4, wherein a retention device 10 comprises of an inner tubular shaft 20 surrounding an elongated shank 30 of a fastening tool 40 having a handle 45, and an outer tubular shaft 50 slidably disposed upon the inner tubular shaft 20.

Extending from the distal end 65 of the inner tubular shaft 20 is a clamping gripper 60, which generally comprises a pair of resilient gripping members 62. Each of the gripping members 62 has on its elongated handle 68 an arcuated portion 70 protruding radially outward from a cylindrical axis 75 of the inner tubular shaft 20.

A plurality of resilient u-shaped members 80A is mounted in between the gripping members 62 at the distal end 65 of the gripping members 62. U-shaped members 80A engage the shaft 30 of the fastening tool 40, so that the inner tubular shaft 20 is longitudinally slidable and rotatable about the shank 30.

Inner tubular shaft 20 comprises two inner cylindrical wall portions 310 and 320 of different diameters, which results in a shoulder portion 330. The inner cylindrical wall portion 320, retainably disposed upon the handle 45, includes an oblong cutout section 340. A resilient member 350, having a knob 360 at a free end 365, is mounted on a side 370 of the cutout section 340.

The free end 365 of the resilient member 350 engages a flexible annular flange 410 disposed upon the handle 45 of the fastening tool 40, so that the inner tubular shaft 20 does not fall off from the fastening tool 40. In a disassembly process, the knob 360 is lifted in a direction away from the handle 45 to allow the inner tubular shaft 20 to move and pass over the annular flange 410, so that the inner tubular shaft 20 is subsequently disengaged from the fastening tool 40. If necessary, a releasable fastener 230 is provided for insertion into a threaded opening 225 in the inner cylindrical wall 320.

Fastener 230 prevents the inner tubular shaft 20 from rotating about the handle 45 when the inner tubular shaft 20 needs to be held steady for the smooth relative rotation of the outer tubular shaft 50 and the inner tubular shaft 20. The fastener 230 also engages a longitudinal channel 430 embedded in the handle 45 to secure the inner tubular shaft 20 to the handle 45.

Outer tubular shaft 50 comprises two outer cylindrical wall portions 440 and 450 of unequal diameters, which results in a shoulder portion 460. The outer tubular shaft 50 comprises an internally threaded tapered bore portion 196 and an end bore portion 98 of generally constant thickness. The outer tubular shaft 50 is slidably disposed upon the inner tubular shaft 20.

A segmented annular guiding ridge 250, on the outer surface of the arcuated sections 70 of clamping gripper 60, engages the threaded interior tapered wall 99 of the outer tubular shaft 50. The outer tubular shaft 50 is slid along the inner tubular shaft 20 to come into engagement with the guiding ridge 250 of the clamping gripper 60. The outer tubular shaft 50 is rotated with respect to the inner tubular shaft 20 in a direction denoted by a curved arrow 255 until the distal ends 120 of the clamping gripper 60 are closed. The gripping jaws 78 finally grasp a fastener 140 in the closed position.

The distal ends 120 of the clamping gripper 60 comprises a gripping section 260, adapted to hold the head of the fastener 140 to prevent slipping and to securely grasp the fastener 140 before insertion into a workpiece (not shown).

Figure 5:
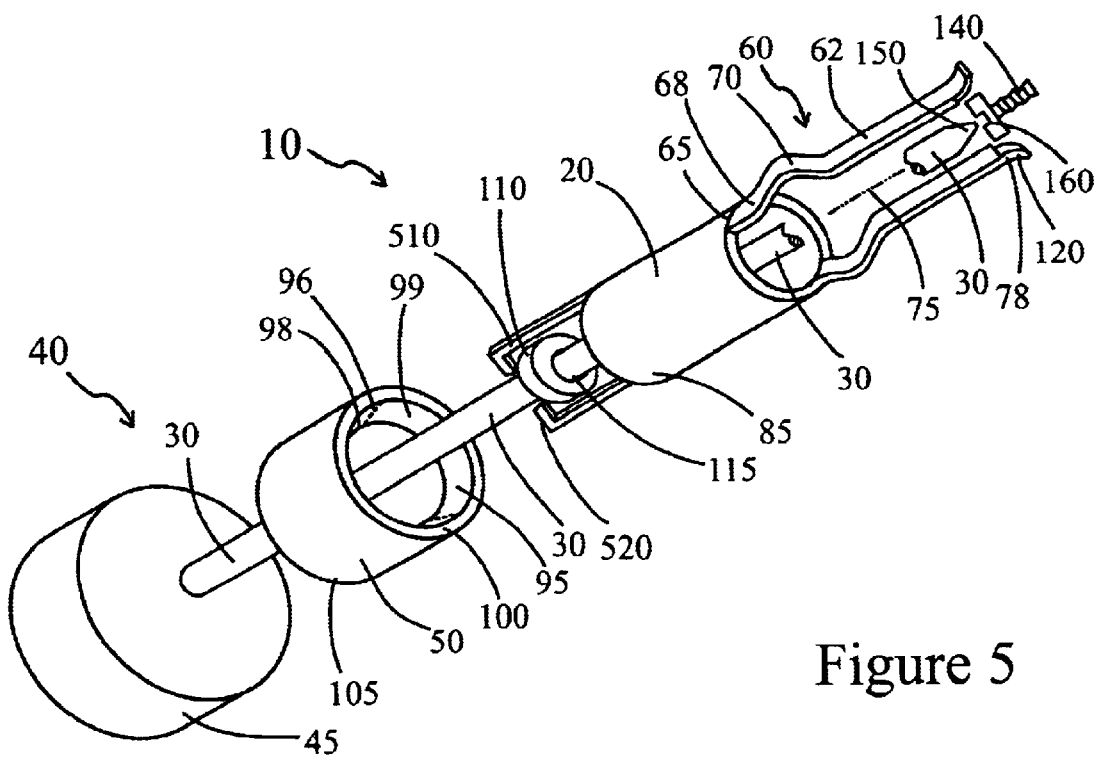
FIG. 5 is a simplified diagram of a fifth preferred embodiment showing a plurality of hooks for engaging an annular flange mounted on the shank of the fastening tool.

Referring now to the fifth preferred embodiment of the invention shown in FIG. 5, wherein a plurality of resilient retaining members 510, in the form of a hook extending from the proximal end 85 of the inner tubular shaft 20, engages an annular flange 110. The annular flange 110 is disposed frictionally upon shank 30 of the fastening tool 40. The free ends 520 of the retaining members 510 are lifted away from shank 30 to allow the clamping gripper 60 to fall off from the fastening tool 40 during a disassembly process.

Figure 6:
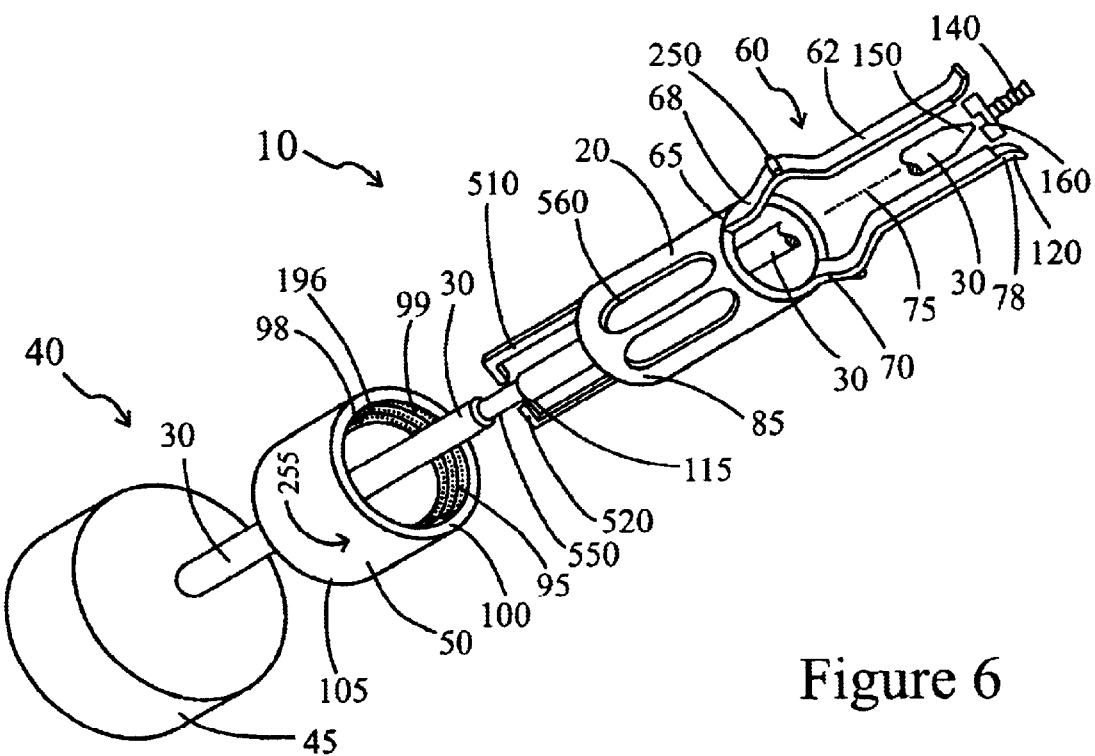
FIG. 6 is a simplified diagram showing a plurality of hooks for engaging an annular recess in the shank of the fastening tool.

Instead of using an annular flange 110, an annular recess 550 is provided in the shank 30 of the fastening tool 40, as shown in FIG. 6. The retaining members 510 mounted on the inner tubular shaft 20 engages the annular recess 550 to prevent the clamping gripper 60 from coming off the fastening tool 40.

Inner tubular shaft 20, having a plurality of generally elongated slots 560 through its body, supports a clamping gripper 60 for engaging a fastener 140 at the distal ends thereof.

Figure 7:
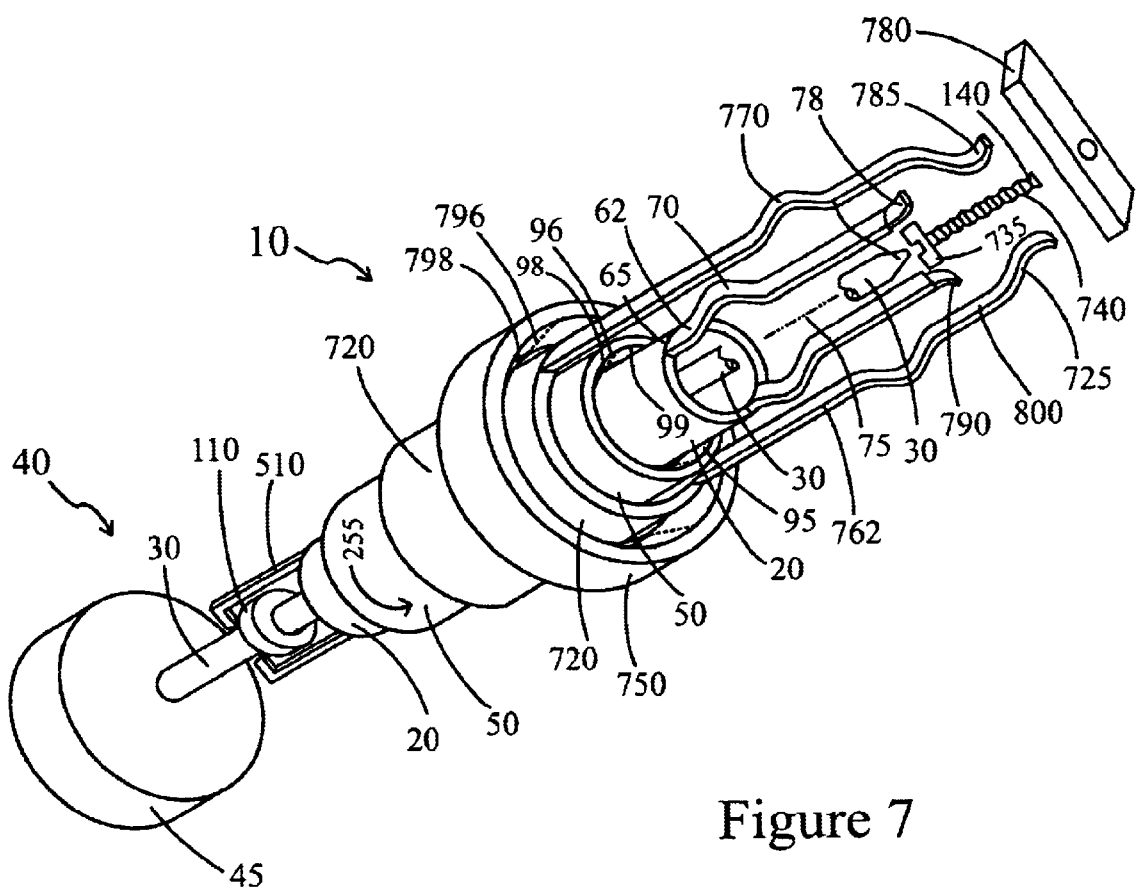
FIG. 7 is a simplified diagram of another preferred embodiment showing a plurality of jaws for engaging the shank and head of the fastener.

Referring now to another preferred embodiment of the invention shown in FIG. 7, wherein a retention device 10 comprises of a first outer tubular shaft 50 slidably disposed upon a first inner tubular shaft 20, and a second outer tubular shaft 750 slidably disposed upon a second inner tubular shaft 720. The second inner tubular shaft 720 in turn, is longitudinally slidable and rotatable about the first outer tubular shaft 50. Extending from the distal end 65 of the inner tubular shaft 20 is a first set of a plurality of gripping members 62, which comprise a plurality of jaw members 78 for engaging the head 735 of a fastener 140.

The first outer tubular shaft 50 comprises a conically tapered bore portion denoted by dashed lines 96 and a substantially uniform end bore portion 98.

Similarly, the second outer tubular shaft 750 comprises a conically tapered bore portion denoted by dashed lines 796 and a substantially uniform end bore portion 798.

Extending from the distal end of the second inner tubular shaft 720 is a second set of a plurality of gripping members 762 for engaging the shank 740 of the fastener 140. Gripping members 62 and 762, each having respectively an arcuated portion 70 and an arcuated portion 770 protruding separately outwardly from the cylindrical axis 75, are arranged circumferentially with axial symmetry about the cylindrical axis 75 of the inner tubular shaft 20. The first outer tubular shaft 50 is slid forward towards the gripping jaws 78, the inner cylindrical tapered wall 99 of the first outer tubular shaft 50 comes into contact with the arcuated portion 70 and presses inwardly the arcuated portion 70 of the gripping members 62 towards the cylindrical axis 75 of the first inner tubular shaft 20 to thereby engage the head 735 of the fastener 140.

Similarly, the second outer tubular shaft 750 presses inwardly the arcuated section 770 of the second inner tubular shaft 762, thereby engaging the shank 740 of fastener 140. Fastener 140 is held at multiple contact points by both the gripping jaws 78 and the end portions 725 of gripping members 762 for insertion into the workpiece 780, preventing undesirable inclination of the fastener 140 to the surface of the workpiece 780.

When the fastener 140 has advanced sufficiently into the workpiece 780, the end portions 785 of the gripping members 762 come into contact with the surface of the workpiece 780. End portions 785 of the gripping members 762 are bent and spread radially outwardly and moved away from the cylindrical axis 75 as the fastener 140 continues to advance into the workpiece 780. At the same time, second inner tubular shaft 720, on which the gripping members 762 are mounted, has the tendency to slide longitudinally towards the handle 45 of the fastening tool 40, until the tips 790 of the gripping members 62 come into engagement with the inner surface 800 of the gripping members 762. The tips 790 of the gripping members 62, protruding outwardly from the cylindrical axis 75, help to ensure that the end portions 785 of the gripping members 762 are subsequently disengaged by pushing the gripping members 762 away from the shank 740 of fastener 140.

The functions of the retaining members 510 and the annular flange 110 in the diagram are described in detail in the foregoing embodiments.

Having described the invention and its preferred modes of operation insufficient detail for those of normal skill in the art to practice the same, it will be obvious to such practitioners to make certain changes and variation in the specific elements of the disclosed embodiments without departing from the scope of the invention. For example, the u-shaped members 80A and 80B shown in the diagram for engaging the shank 30 of the fastening tool 40 can assume many other shapes. Furthermore, they are not necessary needed in the operation and are not the essential elements for the gripping operation. They are needed only for use with various elongated shanks 30 of a variety of sizes now available in the markets.

It is clear that the foregoing disclosure is merely illustrative of the principles of the present invention. Numerous alternatives, modifications and additions, apparent to those skilled in the art, may be made without departing from the spirit and broader aspects of this invention as defined in the appended claims.

What is claimed is:

1. A device defining a retention means for retaining a fastener for use in combination with a fastening tool having a shank and a driver head adapted to engage said fastener, comprising:

a) a clamping gripper having a pair of gripping members, each of which having an arcuated portion protruding outwardly from a central axis of said device, said gripping members being movable resiliently toward said central axis for engagement with said fastener;

b) an inner tubular shaft mounting said clamping gripper to retainably dispose upon said shank of said fastening tool; and c) an outer tubular shaft having an inner tapered through bore for pressing inwardly said arcuated portions of said gripping members;

wherein said outer tubular shaft slides along said inner tubular shaft to which said gripper is attached until wall surface of said inner tapered through bore engages arcuate portion of said gripping members, thereby moving opposing gripping jaws of said gripper toward said central axis to finally grasp said fastener at the distal ends thereof from an initial open position to a final closed position.

2. The device of claim 1, wherein portion of said tapered through bore in said outer tubular shaft is internally threaded.

3. The device of claim 2, wherein said device includes a segmented annular guiding ridge on said gripping member for engagement with internally threaded tapered through bore in said outer tubular shaft.

4. The device of claim 1, wherein said clamping gripper comprises a plurality of said gripping members arranged circumferentially with axial symmetry about said central axis.

5. The device of claim 1, wherein said device comprises a plurality of outer tubular shafts for moving inwardly said gripping members towards said central axis.

6. The device of claim 1, wherein said device includes a restraining means for engagement with a resilient member mounted on said clamping gripper to prevent said clamping gripper from falling off from said fastening tool.

7. The device of claim 1, wherein said device includes a recess in said device for engagement with a resilient member mounted on said clamping gripper to prevent said clamping gripper from falling off from said fastening tool.

8. The device of claim 1, wherein said device includes a locking fastener retainably insertable into enclosing wall of said inner tubular shaft to engage a longitudinal channel of said fastening tool to prevent relative rotation of said inner tubular shaft and said fastening tool.

9. The device of claim 1, wherein said clamping gripper comprises a plurality of said gripping members arranged circumferentially with axial symmetry about said central axis.

10. A device defining a retention means for retaining a fastener for use in combination with a fastening tool having a shank and a driver head adapted to engage said fastener, comprising:

a) a clamping gripper having a pair of gripping members, each of which having an arcuated portion protruding outwardly from a central axis of said device, said gripping members being movable resiliently towards said central axis for engagement with said fastener;

b) an inner tubular shaft mounting said clamping gripper to retainably dispose upon said shank of said fastening tool; and c) an outer tubular shaft having an inner tapered through bore for pressing inwardly said arcuated portions of said gripping members, thereby moving said gripping members towards said central axis to finally grasp said fastener at the distal ends thereof in a closed position; wherein portion of said tapered through bore in said outer tubular shaft is internally threaded.

11. The device of claim 10, wherein said device includes a segmented annular guiding ridge on said gripping member for engagement with internally threaded tapered through bore in said outer tubular shaft.

12. The device of claim 10, wherein said device includes a restraining means for engagement with a resilient member mounted on said clamping gripper to prevent said clamping gripper from falling off from said fastening tool.

13. The device of claim 10, wherein said device includes a recess in said device for engagement with a resilient member mounted on said clamping gripper to prevent said clamping gripper from falling off from said fastening tool.

14. The device of claim 10, wherein said device comprises a plurality of outer tubular shafts for moving said gripping members inwardly towards said central axis.

15. A device defining a retention means for retaining a fastener for use in combination with a fastening tool having a shank and a driver head adapted to engage said fastener, comprising:

a) a clamping gripper having a pair of gripping members, each of which having an arcuated portion protruding outwardly from a central axis of said device, said gripping members being movable resiliently towards said central axis for engagement with said fastener;

b) an inner tubular shaft mounting said clamping gripper to retainably dispose upon said shank of said fastening tool;

c) an outer tubular shaft having an inner tapered through bore for pressing inwardly said arcuated portions of said gripping members, thereby moving said gripping members towards said central axis to finally grasp said fastener at the distal ends thereof in a closed position; and d) restraining means for retaining said clamping gripper to said device.

16. The device of claim 15, wherein said restraining means includes a resilient member mounted on said clamping gripper to prevent said clamping gripper from falling off from said fastening tool.

17. The device of claim 15, wherein said restraining means includes a recess in said device for engagement with a resilient member mounted on said clamping gripper to prevent said clamping gripper from falling off from said fastening tool.

18. The device of claim 15, wherein said fastening tool includes a longitudinal channel for engagement with a locking fastener.

\* \* \* \* \*